United States Patent [19]

Young et al.

[11] Patent Number: 5,382,726

[45] Date of Patent: Jan. 17, 1995

[54] CATALYST AND PROCESS FOR OXYCHLORINATION OF ETHYLENE TO EDC

[75] Inventors: George H. Young, League City, Tex.; Joseph A. Cowfer, Medina; Victor J. Johnston, Silver Lake, both of Ohio

[73] Assignee: The Geon Company, Independence, Ohio

[21] Appl. No.: 156,142

[22] Filed: Nov. 22, 1993

Related U.S. Application Data

[62] Division of Ser. No. 920,721, Jul. 28, 1992, Pat. No. 5,292,703.

[51] Int. Cl.$^6$ .................................. C07C 17/156
[52] U.S. Cl. ................................. 570/243; 570/245; 502/341; 502/346
[58] Field of Search ............... 570/243, 245; 502/341, 502/346

[56] References Cited

U.S. PATENT DOCUMENTS

| | | |
|---|---|---|
| 3,205,280 | 9/1965 | Wattimena et al. |
| 4,446,249 | 5/1984 | Eden . |
| 4,587,230 | 5/1986 | Cavaterra et al. .................. 502/225 |
| 4,740,642 | 4/1988 | Eden et al. ........................... 502/228 |
| 4,740,644 | 4/1988 | Eichhorn et al. .................... 570/243 |
| 4,753,914 | 6/1988 | Eichhorn et al. .................... 502/225 |
| 5,292,703 | 3/1994 | Young et al. ........................ 502/302 |

FOREIGN PATENT DOCUMENTS

| | | | |
|---|---|---|---|
| 0257561 | 8/1987 | European Pat. Off. ............ | 502/225 |
| 012378 | 5/1981 | WIPO . | |

*Primary Examiner*—Anthony Mc Farlane
*Attorney, Agent, or Firm*—William F. Prout; Miles B. Dearth

[57] ABSTRACT

The subject invention relates to catalyst compositions for oxychlorination of ethylene to produce 1,2-dichloroethane. The catalysts comprise copper chloride, at least one alkali metal, at least one rare earth metal, and at least one Group IIA metal on a high surface area support for fluid bed applications or on a high or low surface area support for fixed bed applications. The catalyst compositions are prepared by depositing the metals on a support. The use of the catalyst compositions of the invention in the oxychlorination of ethylene to EDC results in high percent ethylene efficiency, high EDC product purity and high percent HCl conversion without exhibiting catalyst stickiness. A process for oxychlorination of ethylene to produce 1,2-dichloroethane is also disclosed. The process relies on contacting a mixture of ethylene, oxygen or oxygen containing gas and hydrogen chloride with a fixed or fluidized catalyst composition in a reaction zone and recovering 1,2-dichloroethane from the effluents of the reaction zone.

20 Claims, 3 Drawing Sheets

Figure 1. EDC Selectivity vs Temperature.

Figure 2. HCl conversion vs. Temperature

Figure 3. Triane Selectivity vs Temperature

CATALYST AND PROCESS FOR OXYCHLORINATION OF ETHYLENE TO EDC

This is a divisional application of co-pending Ser. No. 07/920,721 filed Jul. 28, 1992, now U.S. Pat. No. 5,292,703.

BACKGROUND OF THE INVENTION

The subject invention relates to fluid or fixed bed catalytic oxychlorination of ethylene to produce 1,2-dichloroethane, commonly called ethylene dichloride (EDC) and relates specifically to improved copper catalysts and their use in ethylene oxychlorination reactions.

Catalysts for the production of chlorinated hydrocarbons by oxychlorination have been well established for a number of years. Conversion of ethylene ($C_2H_4$) to 1,2-dichloroethane by oxychlorination is practiced in commercial installations throughout the world. The preferred method is a vapor phase reaction, over a fluidized catalyst bed, of a mixture of ethylene, hydrogen chloride (HCl) and oxygen or an oxygen containing gas (e.g., air). An example of the conditions required are described in U.S. Pat. No. 3,488,398 to Harpring et al.

A typical catalyst used in oxychlorination reactions comprises about 4% to 17% by weight of a copper compound. Typically, the copper compound is cupric chloride, as the active catalytic ingredient, deposited on particles of a fixed fluidizable support, such as silica, kieselguhr, clay, fuller's earth, or alumina. For use in non-fixed bed catalysis, the support should be readily fluidizable without excessive catalyst loss from the reaction zone, and have proper particle density, resistance to attrition and particle size distribution to be useful in the process. In oxychlorination processes most closely aligned to the present invention, an alumina support is employed which may be gamma alumina, alpha alumina, the so-called microgel aluminas or other forms of "activated" alumina. The standard fixed and fluid bed alumina-based oxychlorination catalysts can be improved upon in significant respects.

It is desirable for the oxychlorination catalyst to effect the highest possible yield of EDC based on ethylene (i.e., for the ethylene to be more completely converted to EDC, with less ethylene being reacted to carbon oxides or higher chlorinated materials). In the high volume business of manufacturing EDC, small increases in the efficiency of ethylene conversion to EDC are very valuable. For example, in a one billion pound per year EDC oxychlorination plant, an ethylene efficiency increase of only 1% can result in a savings of from about 0.5 to about 1.0 million dollars annually. Further, increased ethylene efficiency reduces the amount of by-products produced and the associated potential of release of hydrocarbons and chlorinated hydrocarbons to the environment.

Further, it is becoming much more desirable, for economic and environmental reasons, for the oxychlorination catalyst to also effect a high conversion of the hydrogen chloride (HCl) used in the reaction. Problems can arise when a higher than theoretical molar ratio of HCl to ethylene is used in an attempt to achieve higher ethylene conversions to EDC. Unconverted HCl must be neutralized using, for example, a caustic solution, and the resulting salt must be disposed. Also, higher levels of HCl in the process can lead to higher HCl "break through" downstream of the reactor which can cause corrosion problems. Hence, a modern oxychlorination process will attempt to operate at an HCl to ethylene molar ratio as close to, but not exceeding, the theoretical level of two-to-one (2:1) as possible in conjunction with high HCl conversion. In commercial practice in which ethylene is passed through/over the catalysts one time, the ratio is generally from about 1.93 to about 1.97. In the process where the unreacted ethylene is separated and then recycled, a lower ratio of from about 1.88 to about 1.92 can be employed. In either application, a combination of high HCl conversion and high ethylene efficiency is most desirable.

Lastly, typical cupric chloride on alumina fluid bed catalysts may exhibit a tendency to develop "stickiness" during the oxychlorination reaction at HCl to ethylene molar feed ratios greater than about 1.9. Catalyst stickiness, which is basically agglomeration of catalyst particles, may be a critical barrier to achieving optimum ethylene and HCl feedstock efficiencies in a fluid bed oxychlorination process. The highest ethylene efficiency from an oxychlorination catalyst requires operation with an HCl ethylene molar feed ratio approaching, but not exceeding, the stoichiometric value of 2.0. However, as the HCl ethylene feed ratio is increased above about 1.9 in a commercial process, standard fluid bed oxychlorination catalysts may become progressively more sticky. With increased catalyst stickiness, heat transfer characteristics of the fluid bed worsen, hot spots develop within the catalyst bed, feedstock conversions and yields decline, and, in extreme cases, the bed actually collapses and slumps, causing vapor channel passages through the bed. In commercial operation, upsets to the feedstocks, temperature variations, etc., can lead to an HCl ethylene ratio above the preferred ratio; therefore, a high performance oxychlorination catalyst requires the ability to operate over a wide range of HCl ethylene feed ratios (1.85–2.2). Other requirements for high performance catalysts are excellent fluidization and high conversions, yields, and efficiencies. This problem of catalyst stickiness and a device and means for its partial control are described in U.S. Pat. No. 4,226,798 issued to Cowfer et al. A method of controlling stickiness in standard oxychlorination catalysts is also described in U.S. Pat. No. 4,339,620, also issued to Cowfer et al. Although these devices and methods are helpful, it is more practical and efficient to employ an oxychlorination catalyst which does not develop stickiness during the reaction.

There are references which disclose the use of alkali metals, alkaline earth metals, or rare earth metals along with copper chloride. Although these catalysts are closer in composition to those of the present invention, improvements in composition and performance can still be obtained. None of these references teach or suggest the types and amounts of metals used to improve catalyst performance. Much effort has been put into the improvement of catalysts for oxychlorination of ethylene to form EDC. Due to the large volume of product produced, a small increase in efficiency can produce a large return in cost savings. Increasing the HCl conversion and ethylene efficiency will prove beneficial to the environment as well.

Much effort has been put into developing improved catalysts for oxychlorination reactions. It is worthwhile to note the references most closely aligned with the catalyst and process of the present invention are U.S. Pat. No. 4,740,642 to Eden et al and U.S. Pat. No. 3,205,280. U.S. Pat. No. 4,740,642 relates to a catalyst composition comprising copper, an alkali metal salt and a rare earth metal salt. U.S. Pat. No. 3,205,280 discloses a catalyst composition of an $Al_2O_3$ support (calcined at 900° C. which substantially lowers its surface area) having thereon an alkali metal such as potassium chloride, and/or an alkaline earth metal, a transition metal such as copper, and/or a rare earth metal such as didymium. Both references require specific and limited ratios of alkali or alkaline earth metal to transition or rare earth metals.

The catalysts of the present invention are evaluated based upon a number of criteria: ethylene efficiency, ethylene conversion, HCl conversion, EDC selectivity, carbon dioxide and carbon monoxide selectivity, triane (1,1,2-trichloroethane) selectivity and fluidization quality for fluid bed catalysts. Ethylene and HCl conversion is simply a determination of the amount in mole % of reactant consumed in the reactor. The selectivity is the mole percent yield of pure product formed. The ethylene efficiency is the product of the ethylene conversion and the EDC selectivity, e.g., a 99% ethylene conversion and a 95% EDC selectivity would result in a 94% ethylene efficiency. Small increases in ethylene efficiency, as low as 0.5%, can result in a very large savings due to the large volume of product produced. Also, the reduction of wastes, e.g., over chlorinated by-products, such as triane (1,1,2-trichloroethane), can represent a big savings. These materials currently can cost a producer as much as $500 per ton to dispose in an environmentally safe manner. Therefore, reducing this by-product can save money as well as reduce the potential for pollution.

SUMMARY OF THE INVENTION

The catalyst compositions of the present invention comprise copper chloride, at least one alkali metal, at least one rare earth metal, and at least one Group IIA metal. The catalyst compositions are prepared by depositing the metals on the support. The use of the catalyst compositions of the invention in the oxychlorination of ethylene to EDC results in high percent ethylene efficiency, high EDC product purity and high percent HCl conversion without exhibiting catalyst stickiness. Furthermore, all of these catalyst performance benefits are obtained simultaneously without any need to sacrifice one benefit for another.

DETAILED DESCRIPTION OF THE INVENTION

Figure 1:
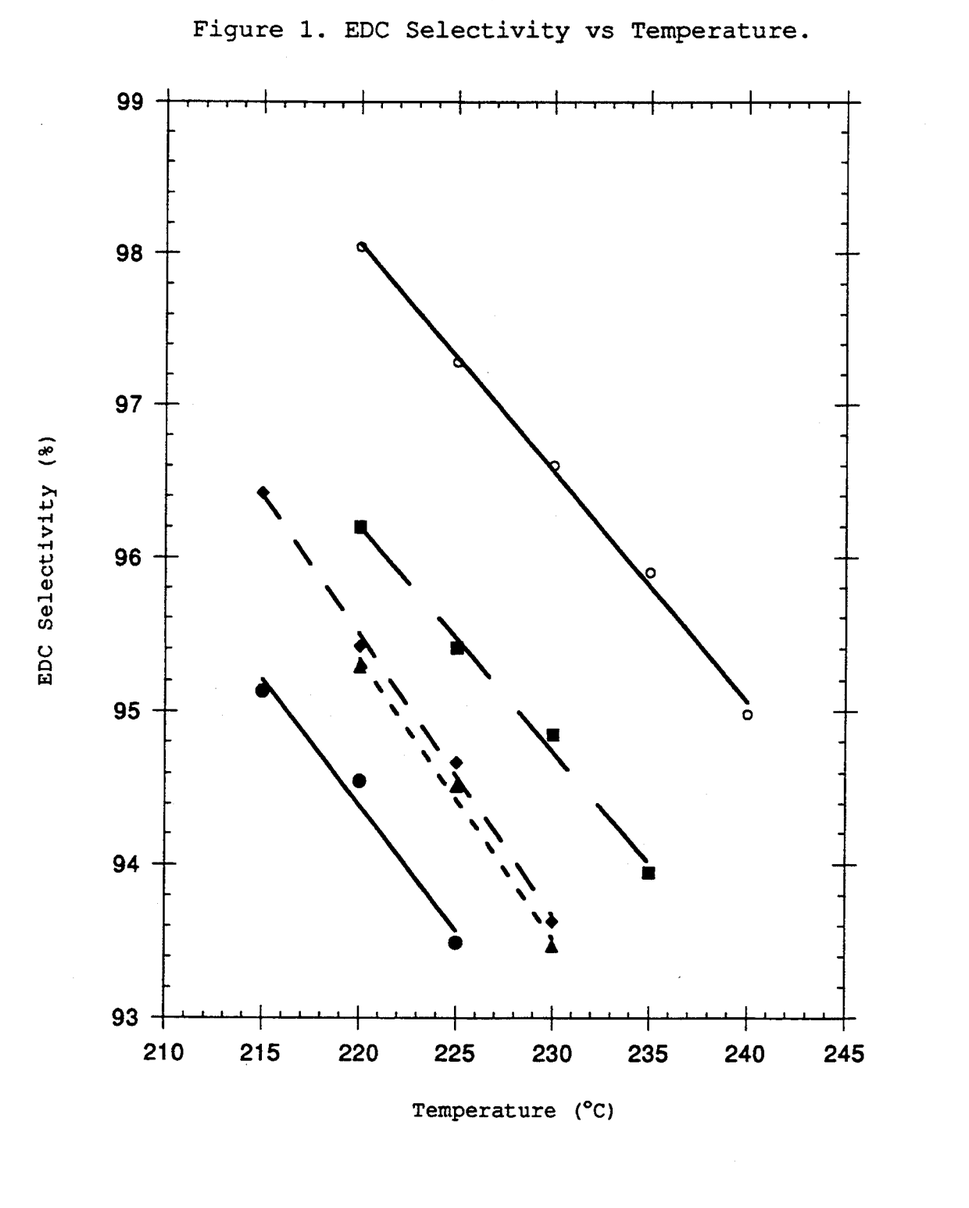
FIGS. 1, 2 and 3 are graphs of ethylene dichloride (EDC) selectivity versus temperature, HCl conversion versus temperature and triane (by-product) selectivity versus temperature, respectively, for four (4) prior art catalysts and the catalyst of the subject invention. All catalysts have about 5% copper metal deposited as the dichloride. The first catalyst (●) is copper alone on an alumina support. The second catalyst (▲) is copper with magnesium added. The third catalyst (♦) is copper, barium and potassium. This represents a catalyst composition disclosed in U.S. Pat. No. 4,446,249 to Eden. The fourth catalyst (■) is copper, potassium and a mixture of rare earth metals. This represents a catalyst composition disclosed in U.S. Pat. No. 4,740,642 to Eden, et al. The final set of data (o) is for the catalyst of the subject invention.
Figure 2:
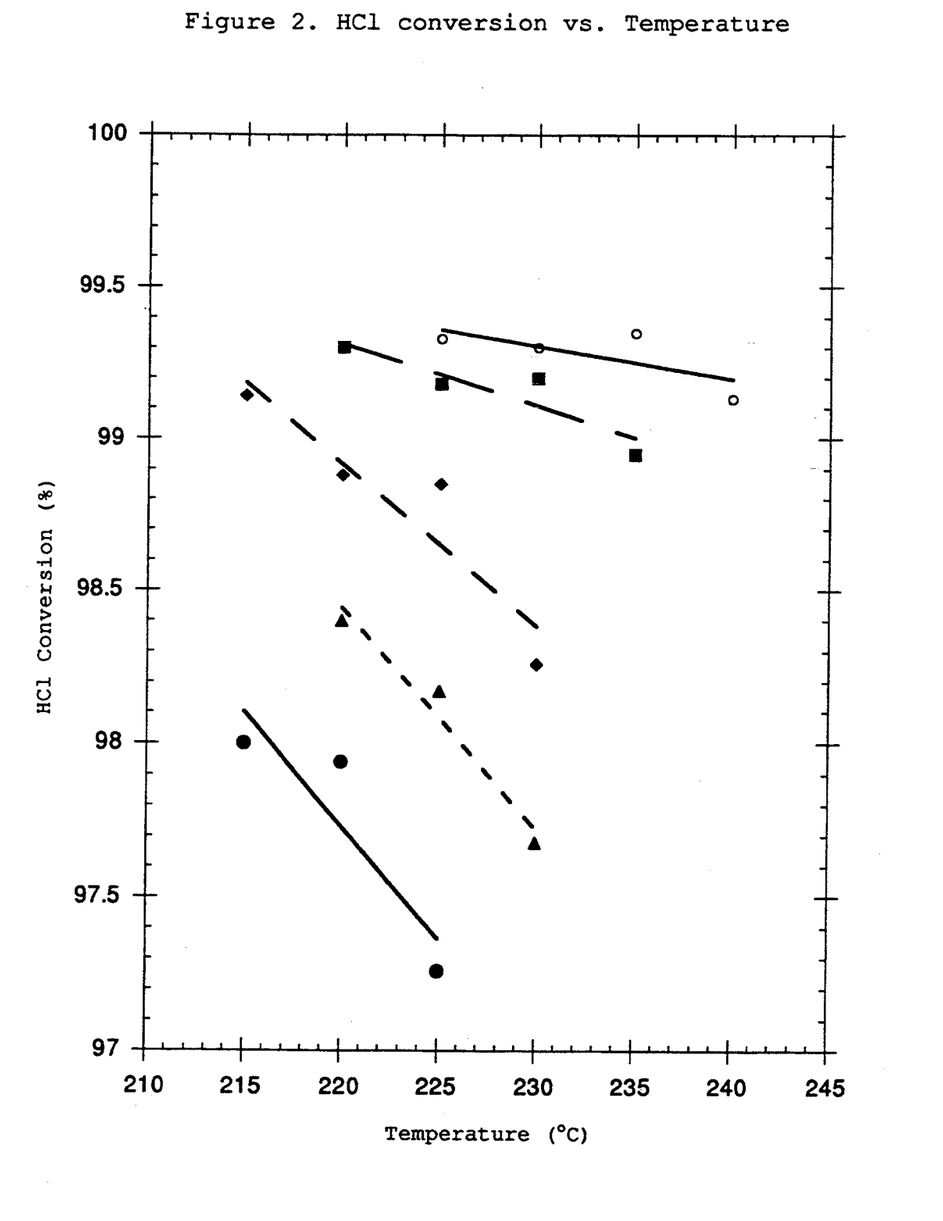
Figure 3:
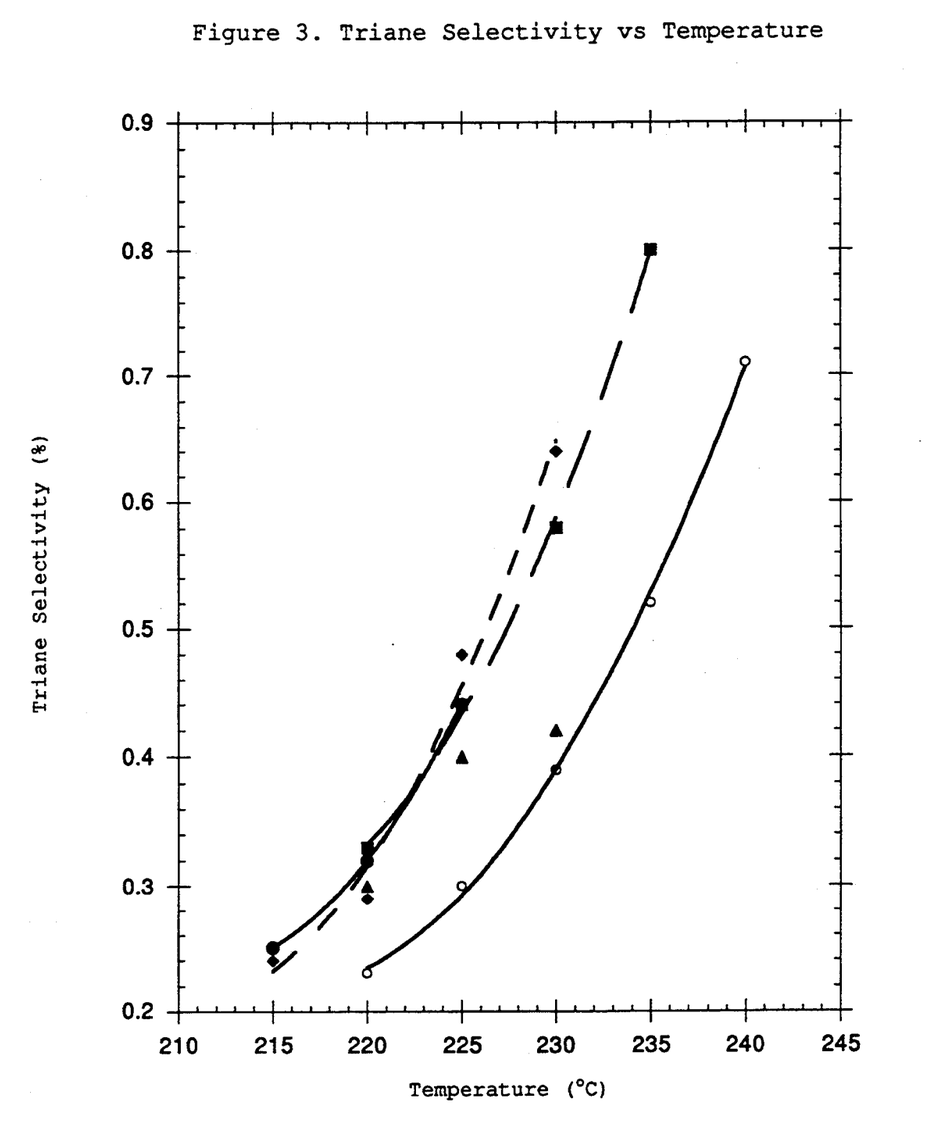

The catalyst compositions of this invention employ support materials which are readily available. For fluid bed catalysis, the metals should be deposited on high surface area supports. The principle reason for the requirement of high surface area supports in fluid bed catalysis is the necessity to reduce the stickiness of the catalyst as the metal can be dispersed over a large area. In fixed bed catalysis, the support can have either high or lower surface area. Examples of support materials include but are not limited to materials such as silica, magnesia, kieselguhr, clay, fuller's earth, alumina or combinations thereof. The preferred catalytic process is fluid bed catalysis using a high surface area support and the invention, for simplicity and convenience, will be described in connection therewith, it being understood that this is merely intended in an illustrative sense and not limitative.

Examples of fluidizable high surface area supports include but are not limited to materials such as silica, magnesia, kieselguhr, clay, fuller's earth, alumina or combinations thereof. The preferred supports are high surface area aluminas (often referred to as γ-alumina). The invention will be described hereinafter in terms of alumina supports. This is meant to be illustrative and not limiting. The fluidizable alumina support material has a surface area in the range of about 30 to 250 $m^2/g$, a compacted bulk density in the range of 0.8 to 1.1 grams per cc, a pore volume in the range of 0.2 to 0.5 cc per gram and a particle size distribution such that about 70 to 95 weight percent of the particles are below 80 microns in diameter, about 30 to 50 percent are below 45 microns in diameter, and about 15 to 30 percent are below 30 microns in diameter, with no more than 5% by weight of the particles larger than 200 microns and no more than 10% by weight of the particles smaller than 20 microns. Such alumina support materials are readily fluidizable, relatively stable, mechanically strong and resistant to attrition.

It is recognized that some alumina support materials may contain in addition to aluminum oxide ($Al_2O_3$) small amounts of other metals such as metal oxides like sodium oxide, magnesium oxide, etc. These alumina supports are readily useable in this invention.

The alkali metal employed in the present invention can be sodium, potassium, lithium, rubidium, or cesium, or a mixture of one or more such metals. The alkali metal is used in the form of a water soluble salt, and preferably is used in the form of an alkali metal chloride. However, other alkali metal salts that would convert to the chloride salt during the oxychlorination process can also be used, such as the carbonate salt or other halide salts like the bromide salts. The alkali metal is used in the range from about 0.2% to about 2.0% by weight (as the metal) based on the total weight of the catalyst composition. The preferred alkali metals are potassium, lithium, and cesium. The most preferred alkali metal is potassium, and the preferred alkali metal salt is potassium chloride. The minimum amount of alkali metal required is about 0.2%. The preferred minimum amount of alkali metal is about 0.25% by weight based on the total weight of the catalyst. The most preferred minimum amount of alkali metal is about 0.5% by weight based on the total weight of the catalyst. The preferred maximum amount of alkali metal is about 2.0% by weight based on the total weight of the catalyst. The most preferred maximum amount of alkali metal is about 1.5% by weight based on the total weight of the catalyst.

The rare earth metal employed in the invention can be any of the elements listed as elements 57 through 71 of the Periodic Table and the pseudo rare earth elements yttrium and scandium. Examples of rare earth metals include lanthanum, cerium, praseodymium, neodymium, or naturally occurring mixtures of one or more such metals such as didymium. The rare earth metal is used in the form of a rare earth metal chloride. However, other rare earth metal salts which would convert to the chloride during the oxychlorination process can also be used, e.g., carbonate salts, nitrate salts or other halide salts like a bromide salt.

The rare earth metal is used in the range from about 0.1% to about 9% by weight (as the metal) based on the total weight of the catalyst composition. The preferred minimum amount of rare earth metal is about 0.1% by weight based on the total weight of the catalyst. The most preferred minimum amount of rare earth metal is about 0.5% by weight based on the total weight of the catalyst. The maximum amount of rare earth metal is about 9% by weight based on the total weight of the catalyst. The preferred maximum amount of rare earth metal is about 6% by weight based on the total weight of the catalyst. The most preferred maximum amount of rare earth metal is about 3% by weight based on the total weight of the catalyst. Typically, the rare earth metal employed is cerium or didymium in the form of chloride salts.

Surprisingly, it has been discovered that utilizing a rare earth metal mixture wherein the mixture is predominantly lanthanum and cerium and the percentage of lanthanum is greater than the percentage of cerium will provide a catalyst with increased activity. This increased catalyst activity gives improved EDC selectivity because the percent ethylene conversion can be maintained at a lower operating temperature. The preferred ratio of the percentage of lanthanum to the percentage of cerium is at least 2.0. If it is desirable to operate at higher temperatures, the catalyst composition using a mixture of rare earth metals employed should have the percentage of cerium greater than the percentage of lanthanum.

The Group IIA metals are magnesium, calcium, strontium, and barium. Preferably, the Group IIA metals are magnesium and barium. The most preferred Group IIA metal is magnesium. The preferred minimum amount of Group IIA metal is about 0.05% by weight as the metal based on the total weight of the catalyst. The most preferred minimum amount of Group IIA metal is about 0.25% by weight based on the total weight of the catalyst. The preferred maximum amount of Group IIA metal is about 4.0% by weight based on the total weight of the catalyst. A more preferred maximum amount of Group IIA metal is about 3.0% by weight based on the total weight of the catalyst. The most preferred maximum amount of Group IIA metal is about 2.0%.

The metal salts can be added onto the support by addition of a solution of the salt in any suitable solvent. While any metal salts capable of forming a solution are suitable, the preferred metal salts are the chloride salts. The preferred solvent is water.

One method of addition of the metals onto the alumina support is accomplished by impregnating the support with an aqueous solution of a water soluble salt of the metals along with a water soluble salt of the copper compound and then drying the wetted support. The alkali metal(s), rare earth metal(s) and Group IIA metal(s) could be but do not have to be calcined on the support prior to deposition of the copper compound to produce a fluidizable catalyst.

It was discovered that only particular ranges of loadings of copper, alkali metal(s), rare earth metal(s) and Group IIA metal(s) would result in all of the high performance characteristics described above. Outside of the particular loadings of the active metals, high performance in all respects is not achieved.

The copper compound is also used in the form of a water soluble salt, and preferably is used in the form of cupric chloride. However, other copper salts that could convert to the chloride during the oxychlorination process can also be used, such as the nitrate salt, carbonate salt or other halide salts like the bromide salt. The copper salt is deposited on the alumina support using the same techniques as described above. The amount of copper metal deposited is based on the activity desired and the specific fluidization characteristics of the support for fluid bed catalyst applications. The amount of copper metal employed is in the range from about 2% by weight to about 8% by weight as copper metal or, for example, from about 4% to about 17% by weight as the copper (II) chloride salt, both based on the total weight of the catalyst composition. The preferred copper salt is copper chloride. The preferred minimum amount of copper metal is from about 2.0% by weight based on the total weight of the catalyst. The most preferred minimum amount of copper metal is about 3.0% by weight based on the total weight of the catalyst. The preferred maximum amount of copper metal is about 8.0% by weight based on the total weight of the catalyst. The most preferred maximum amount of copper metal is about 6.0% by weight based on the total weight of the catalyst. If the copper is determined as the copper II chloride salt, then the minimum amount of copper salt is about 4.0% by weight based on the total weight of the catalyst. The most preferred minimum amount of copper salt is about 6.0% by weight based on the total weight of the catalyst. The preferred maximum amount of copper salt (as the copper II chloride) is about 17% by weight based on the total weight of the catalyst. The most preferred maximum amount of copper salt is about 13% by weight based on the total weight of the catalyst. The final catalyst composition containing the alkali metal(s), rare earth metal(s), Group IIA metal(s) and copper compound is readily fluidizable.

The specific characteristics such as surface area and pore volume, for example, are, of course, modified by reason of the deposit of the metal salts. Hence, the catalyst compositions of this invention have a final surface area in the range of about 20 to about 220 m$^2$/g, which is about 10% to 30% lower than that of the alumina support before the deposit of the metals. The preferred range of surface areas for fluid bed catalysts is about 70 to about 170 m$^2$/g. The most preferred range of surface area for fluid bed catalysts is from about 80 to about 130 m$^2$/g.

Other metals can be present in the catalyst compositions of the invention in relatively small amounts. For example, alkaline earth metals and/or transition metals can be present in up to about 1% by weight total based on the total weight of the catalyst composition. Examples of such other metals are iron, zinc, lead, and the like.

The catalyst compositions of this invention are readily prepared by wetting the alumina support material, as above described, with an aqueous solution of a salt(s) of the desired metals. The wetted alumina is then dried slowly at about 80° C. to 150° C. to remove water. An amount of the metal salt is chosen so that the final catalyst contains from about 2% to about 8% by weight of copper, from about 0.2% to about 2.0% by weight of the incorporated alkali metal and from about 0.1% to about 9% by weight of the rare earth metal, and from about 0.05% to about 4.0% by weight of Group IIA metal, all metals based on the total weight of the catalyst composition. The metal salt used in the aqueous solution can be in the form of any water soluble salt such as previously described, like the chloride or carbonate salt of potassium, sodium, lithium, rubidium or cesium, or of lanthanum, cerium, praseodymium, neodymium, and didymium (which is a mixture of rare earth metals which contains praseodymium and neodymium together) and of magnesium, barium, calcium, or strontium and of copper. It should be noted that for fixed bed catalysis the percentages of the metals and total weight can be increased as catalyst stickiness is not a critical factor.

The subject invention also contemplates a process for oxychlorination of ethylene to form ethylene dichloride (EDC). The process comprises contacting ethylene, oxygen or an oxygen containing gas and hydrogen chloride (HCl) with a catalyst composition in a reaction zone and recovering the effluent of the reaction zone. The catalyst employed comprises copper, alkali metal(s), rare earth metal(s) and Group IIA metal(s). The metals are deposited on a high surface area support for fluid bed applications or on a high or low surface area support for fixed bed applications.

This process can be carried out as a once through process wherein any unreacted ethylene is vented or otherwise removed, or in a recycle process wherein the unreacted ethylene is recycled back into the reactor. In the recycle process the ratio of HCl to ethylene will tend to be lower at a molar ratio of about 1.88 to about 1.92.

The catalyst compositions of the invention are highly efficient catalysts for the oxychlorination of ethylene to EDC. The reaction process temperatures vary from about 190° C. to about 260° C., and more preferably from about 220° C. to 250° C. Reaction pressures vary from atmospheric to as high as about 200 psig. Contact times in the fluid bed and fixed bed catalysis can vary from about 10 seconds to about 50 seconds (contact time is defined here as the ratio of reactor volume taken up by the catalyst to the volumetric flow rate of the feed gases at the reactor control temperature and top pressure), and more preferably are from about 20 to 35 seconds. The ratio of the ethylene, HCl, and oxygen reactants, based on the moles of HCl fed to the reactor, range from about 1.0 to about 1.1 moles of ethylene and about 0.5 to about 0.9 mole of oxygen per 2.0 moles of HCl. As previously mentioned, modern oxychlorination processes attempt to operate within the stoichiometric ratio of about 1.89 to about 2.0 moles of HCl to 1 mole of ethylene.

When the novel catalyst compositions are used under commercial production conditions in the oxychlorination of ethylene to EDC at a temperature of from about 215° C. to about 260° C. with about a 30 second fluid bed contact time, the conversion of ethylene is 99% or above and the percent ethylene efficiency is above about 96%. This efficiency compares with a normal commercial ethylene efficiency of about 93 up to 95% obtained using conventional, known catalyst compositions. The percent conversion of HCl is also very high using the catalysts of the present invention, exceeding 99% HCl conversion and also exceeding that achieved using conventionally known catalyst compositions. Also, the catalyst compositions of this invention are not "sticky" when used under commercial oxychlorination reaction conditions. Accordingly, this invention provides, in addition to improved catalyst compositions, an improved fluid-bed ethylene to EDC oxychlorination process. The use of the catalyst compositions of this invention in a fluidized or fixed bed oxychlorination process for converting ethylene, hydrogen chloride and oxygen (supplied either as air in a once-through reactor or as oxygen gas in a vent-gas-recycle reactor) to EDC, results in substantial performance improvements over all prior art catalysts which include the combined benefits of higher ethylene efficiency, higher EDC product purity, and higher HCl conversion while maintaining excellent fluidization quality. Furthermore, all of these catalyst performance benefits are obtained simultaneously without any need to sacrifice one benefit for another.

The specific Examples set forth below illustrate the unique and unexpected characteristics of the catalyst compositions of this invention, and are not intended to be limiting of the invention. The Examples particularly point out the criticality of using a combination of copper chloride, rare earth metal(s), alkali metal(s), and a Group IIA metal(s). In all of the Examples, the fluid bed oxychlorination reaction is conducted using a laboratory scale fluid bed reactor. The reactor volume, the amount of catalyst charged to the reactor, the fluid density, the reactant flow rates, the temperature and the pressure all affect the contact time between reactants and catalyst. Reactor height to diameter ratio can also effect reaction conversions, selectivities, and efficiencies. Therefore, in order to insure that measured differences in catalyst performance results are due strictly to inherent differences in catalyst characteristics rather than to differences in reactor geometry or reactor conditions, all catalyst performance evaluations are conducted in virtually identical laboratory scale reactors using the same reaction contact time, the same set of feed conditions, and the same reactor control methods. The reactor is equipped with means for delivering gaseous ethylene, oxygen (as air), and HCl through the reactor zone, means for controlling the quantities of reactants and reaction conditions, and means for measuring and ascertaining the composition of the effluent gases to determine the percent HCl conversion, percent yield of EDC, and percent ethylene efficiency and EDC product purity.

EXAMPLES

The invention will now be illustrated by examples. The examples are not intended to be limiting of the scope of the present invention. In conjunction with the general and detailed description above, the examples provide further understanding of the present invention and demonstrate some preferred embodiments of the invention. Examples I, II, III and IV are for comparison as they describe catalysts which are known and described in the art. Examples V-IX are catalyst compositions of the subject invention.

A series of experiments were performed to show the unique features of the catalyst compositions of the invention. In the experiments, the gaseous reactants, ethylene, oxygen (as air), and hydrogen chloride, were fed to the reactor in molar ratios of 1.0 mole ethylene, 0.8 mole oxygen, and from 1.9 to 2.0 mole hydrogen chloride. The data presented below was obtained with a molar feed ratio in the range of about 1.96 to 1.98 mole hydrogen chloride per mole of ethylene, and are interpolated for purposes of comparison at a constant feed ratio of 1.97 mole hydrogen chloride per mole of ethylene. This allows the catalysts to be compared under identical conditions and as a result the chemical performance differences observed in the examples below reflect inherent differences in catalyst performance and are not due to differences in experimental design.

The reactions were conducted at temperatures in the range of about 215° C. to about 240° C. by passing the reactants through the catalyst bed to form EDC. The temperatures employed for each catalyst were chosen based on where the best performance could be observed by the catalyst. The catalysts used in the experiments each contained about 5% by weight of copper metal (added as cupric chloride) as the primary catalytic metal. The fluidizable alumina support used was a gamma alumina having a surface area of 150 to 165 square meters per gram ($m^2/g$). The metals employed were deposited on the fluidizable alumina support by thoroughly mixing the alumina support with an aqueous solution of the corresponding chlorides; cupric chloride, the alkali metal chloride, the rare earth metal chloride, and the Group IIA metal chloride, followed by drying the wetted mass to fluidity by heating. The fluidizable catalyst composition had a surface area lower than the starting alumina support by a factor of about 10 to 30 percent.

EXAMPLE I

In this example, the catalyst composition employed was 5% copper on a high surface alumina support. No rare earth, alkali or Group IIA metals were employed. The reactions were carried out as temperatures of 215° C., 220° C. and 225° C. The results are shown in Table I.

TABLE I

| Temp | Ethylene Conversion (%) | HCl Conversion(s) | EDC Selectivity (%) | $CO + CO_2$ Selectivity (%) | Triane Selectivity (%) |
|---|---|---|---|---|---|
| 215 | 99.31 | 98.0 | 95.13 | 4.29 | 0.25 |
| 220 | 99.69 | 97.94 | 94.55 | 4.77 | 0.32 |
| 225 | 100.0 | 97.26 | 93.49 | 5.84 | 0.44 |

EXAMPLE II

In this example, the catalyst composition employed was 4.9% copper and 1.6% magnesium on a high surface alumina support. The reactions were carried out at 220° C. 225° C. and 230° C. The results are shown in Table II.

TABLE II

| Temp | Ethylene Conversion (%) | HCl Conversion (%) | EDC Selectivity (%) | $CO + CO_2$ Selectivity (%) | Triane Selectivity (%) |
|---|---|---|---|---|---|
| 220 | 99.34 | 98.40 | 95.29 | 3.90 | 0.30 |
| 225 | 99.60 | 98.17 | 94.52 | 4.60 | 0.40 |
| 230 | 99.91 | 97.68 | 93.47 | 5.29 | 0.42 |

EXAMPLE III

In this example, the catalyst composition employed was as disclosed in U.S. Pat. No. 4,446,249 to Eden. This composition comprised 5% copper, 0.6% barium and 0.5% potassium. The reactions were carried out at temperatures of 215° C., 220° C., 225° C. and 230° C. The results are shown in Table III.

TABLE III

| Temp | Ethylene Conversion (%) | HCl Conversion (%) | EDC Selectivity (%) | $CO + CO_2$ Selectivity (%) | Triane Selectivity (%) |
|---|---|---|---|---|---|
| 215 | 98.92 | 99.14 | 96.42 | 3.02 | 0.24 |
| 220 | 99.55 | 98.88 | 95.42 | 3.92 | 0.29 |
| 225 | 99.96 | 98.85 | 94.67 | 4.57 | 0.48 |
| 230 | 100.0 | 98.26 | 94.63 | 5.20 | 0.64 |

EXAMPLE IV

In this example, the catalyst composition employed was as disclosed in U.S. Pat. No. 4,740,642 to Eden, et al. The catalyst employed had a copper level of 5.0% by weight along with 0.8% alkali metal (potassium) and 2.1% rare earth metal (cerium). The catalysts were prepared and tested in the manner detailed in the Examples above at temperatures of 220° C., 225° C., 230° C. and 235° C. All of the catalysts exhibited good fluidization. The results are shown in Table IV.

TABLE IV

| Temp | Ethylene Conversion (%) | HCl Conversion (%) | EDC Selectivity (%) | $CO + CO_2$ Selectivity (%) | Triane Selectivity (%) |
|---|---|---|---|---|---|
| 220 | 99.20 | 99.30 | 96.2 | 3.15 | 0.33 |
| 225 | 99.54 | 99.18 | 95.41 | 3.75 | 0.44 |
| 230 | 99.82 | 99.20 | 94.85 | 4.12 | 0.58 |
| 235 | 99.99 | 98.95 | 93.95 | 4.68 | 0.80 |

EXAMPLE V

In this example, the catalyst composition employed comprised 4% copper, 1.0% potassium, 2.3% cerium and 1.2% magnesium on a high surface area alumina substrate. The reactions were carried out at temperatures of 220° C., 225° C., 230° C., 235° C. and 240° C. The results are shown in Table V.

TABLE V

| Temp | Ethylene Conversion (%) | HCl Conversion (%) | EDC Selectivity (%) | $CO + CO_2$ Selectivity (%) | Triane Selectivity (%) |
|---|---|---|---|---|---|
| 220 | 97.0  | 98.50 | 98.04 | 1.32 | 0.23 |
| 225 | 98.23 | 99.33 | 97.28 | 1.83 | 0.30 |
| 230 | 98.80 | 99.30 | 96.6  | 2.56 | 0.39 |
| 235 | 99.38 | 99.35 | 95.9  | 3.11 | 0.52 |
| 240 | 99.66 | 99.13 | 94.98 | 3.86 | 0.71 |

EXAMPLE VI

A catalyst composition prepared according to U.S. Pat. No. 4,740,642 (this preparation is similar to Example IV) comprising 4.5% copper, 0.7% potassium and 2.0% of a rare earth metal mixture. This catalyst was then treated with a solution of magnesium chloride so that the magnesium level was 1.2%. The results of these reactions are shown in Table VI.

TABLE VI

| Temp | Ethylene Conversion (%) | HCl Conversion (%) | EDC Selectivity (%) | $CO + CO_2$ Selectivity (%) | Triane Selectivity (%) |
|---|---|---|---|---|---|
| 230 | 98.47 | 99.17 | 96.77 | 2.67 | 0.46 |
| 235 | 98.83 | 98.72 | 95.73 | 3.55 | 0.59 |
| 240 | 99.24 | 98.83 | 95.00 | 4.00 | 0.79 |

EXAMPLE VII

This example is similar to Example V except that a mixture of rare earth metals having a higher percentage of lanthanum was employed. The loadings of metals were as follows: copper 3.9%, potassium 1.0%, mixture of rare earth metals 2.25% and magnesium 1.3%. The rare earth metal mixture was 52% lanthanum, 20% cerium, 21% neodymium and 7% praseodymium. The reactions were carried out at temperatures of 225° C., 230° C., and 235° C. The results are shown in Table VII.

TABLE VII

| Temp | Ethylene Conversion (%) | HCl Conversion (%) | EDC Selectivity (%) | $CO + CO_2$ Selectivity (%) | Triane Selectivity (%) |
|---|---|---|---|---|---|
| 225 | 98.96 | 99.35 | 96.74 | 2.85 | 0.33 |
| 230 | 99.32 | 99.3  | 95.93 | 3.41 | 0.53 |
| 235 | 99.68 | 99.25 | 95.11 | 3.97 | 0.74 |

EXAMPLE VIII

This is similar to Example V except that barium was substituted for magnesium. The loadings of metals were as follows: copper 4% potassium 0.5%, cerium 1.5% and barium 0.7%. The reactions were carried out at several temperatures and the catalysts gave good results in converting ethylene and HCl to EDC.

EXAMPLE IX

This example is similar to Example V except that calcium was substituted for magnesium. The loading of metals was as follows: copper 4.7%, potassium 1.2%, cerium 2.9% and calcium 1.2%. The reactions were carried out at several temperatures and the catalysts gave good results in converting ethylene and HCl to EDC.

The above preferred embodiments and examples are given to illustrate the scope and spirit of the present invention. These embodiments and examples will make apparent, to those skilled in the art, other embodiments and examples. These other embodiments and examples are within the contemplation of the present invention.

Therefore, the present invention should be limited only by the appended claims.

What is claimed is:

1. In the process of oxychlorination of ethylene to produce 1,2-dichloroethane by contacting a mixture of ethylene, oxygen, or oxygen containing gas and hydrogen chloride with a catalyst in a reaction zone and recovering 1,2-dichloroethane from effluents of the reaction zone, the improvement which comprises the use of a catalyst comprising a support having deposited thereon an active metal composition comprising from about 2% to about 8% by weight of copper, from about 0.2% to about 2% by weight alkali metal(s), from about 0.1% to about 9% by weight of rare earth metal(s), and from about 0.05% to about 4% of Group IIA metal(s) selected from the group consisting of magnesium and barium, all weight percents based upon the total weight of said catalyst and wherein said catalyst has a surface area frown about 20 to about 220 $m^2g$.

2. The process of claim 1 wherein the active metal composition[comprising comprises about 3% to about 6% by weight of copper, from about 0.25% to about 1.3% by weight of alkali metal(s), from about 0.5% to about 6% by weight of rare earth metal(s), and from about 0.25% by weight to about 3% by weight of said Group IIA metal(s).

3. The process of claim 1 wherein the metals are deposited on a fluidizable high surface area support.

4. The process of claim 1 wherein the metals are deposited on a support and the catalysis is carried out on a fixed bed.

5. The process of claim 3 wherein the support is an alumina support.

6. The process of claim 1 wherein said Group IIA metal(s) are present in from about 0.25% to about 3%.

7. The process of claim 6 wherein said Group IIA metal(s) are present in from about 0.5% to about 2%.

8. The process of claim 1 wherein the Group IIA metal is magnesium.

9. The process of claim 1 wherein the alkali metal is at least one metal selected from the group consisting of potassium, lithium, sodium, rubidium, and cesium.

10. The process of claim 9 wherein the alkali metal is potassium.

11. The process of claim 1 wherein the rare earth metal is at least one metal selected from the group consisting of lanthanum, cerium, neodymium, praseodymium, yttrium and scandium.

12. The process of claim 11 wherein the rare earth metal is a mixture of cerium, lanthanum, neodymium, and praseodymium, and the percentage of cerium is greater than the percentage of any of the other rare earth metals.

13. The process of claim 12 wherein the rare earth metal is a mixture of lanthanum, cerium, neodymium, and praseodymium and the percentage of lanthanum is greater than the percentage of cerium.

14. The process of claim 13 wherein the rare earth metal is a mixture of lanthanum, cerium, neodymium, and praseodymium and the ratio of the percentage lanthanum to cerium is at least 2:1.

15. The process of claim 1 wherein the alkali metal is potassium, the rare earth metal is cerium, and the Group IIA metal is magnesium.

16. The process of claim 1 wherein the alkali metal is potassium, the rare earth metal is a mixture of lanthanum, cerium, neodymium, and praseodymium and the ratio of lanthanum to cerium is at least 2:1, and the Group IIA metal is magnesium.

17. The process of claim 1 wherein the copper, alkali metal and rare earth metal are deposited on the support prior to depositing of the Group IIA metal.

18. The process of claim 1 further characterized in that the ratio of ethylene, HCl, and oxygen employed range from about 1.0 to about 1.1 moles of ethylene and about 0.5 mole to about 0.9 mole of oxygen for every 2.0 moles of HCl.

19. The process of claim 1 wherein the reactants are passed over the catalyst in a once through process.

20. The process of claim 1 wherein the unreacted ethylene is recycled through the reactor.

* * * * *